United States Patent
Maase et al.

(10) Patent No.: US 7,368,604 B2
(45) Date of Patent: May 6, 2008

(54) METHOD FOR THE PRODUCTION OF ACYLPHOSPHINE OXIDES

(75) Inventors: Matthias Maase, Speyer (DE); Klemens Massonne, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 341 days.

(21) Appl. No.: 10/529,190

(22) PCT Filed: Sep. 12, 2003

(86) PCT No.: PCT/EP03/10150

§ 371 (c)(1), (2), (4) Date: Mar. 24, 2005

(87) PCT Pub. No.: WO2004/029063

PCT Pub. Date: Apr. 8, 2004

(65) Prior Publication Data

US 2006/0052636 A1  Mar. 9, 2006

(30) Foreign Application Priority Data

Sep. 24, 2002 (DE) .............................. 102 44 684

(51) Int. Cl.
*C07F 9/02* (2006.01)
(52) U.S. Cl. .................................... 562/876
(58) Field of Classification Search .................. 562/876
See application file for complete search history.

(56) References Cited

U.S. PATENT DOCUMENTS

| 2,659,747 | A |   | 11/1953 | Young |         |
|-----------|---|---|---------|-------|---------|
| 5,399,770 | A | * | 3/1995  | Leppard et al. | 568/15 |
| 5,472,992 | A |   | 12/1995 | Leppard et al. |        |

FOREIGN PATENT DOCUMENTS

| EP | 0 007 508 A | 2/1980 |
| EP | 0 062 839   | 10/1982 |
| EP | 0 184 095   | 6/1986 |
| JP | 10 120691   | 5/1998 |
| WO | 00/32612    | 6/2000 |

OTHER PUBLICATIONS

Hennig et al., 1987, CAS: 108:37955.*
Lindner et al., 1981, CAS: 95: 115668.*
Al'Fonsov V.A. et al: "S-Acetyl phosphorothioites: synthesis, isomerism, and some reactions" Journal of General Chemistry USSR., vol. 58, No. 8, pp. 1548-1553, Jan. 20, 1989. XP- 002266089.
Sluggett G. W. et al.: "(2,4,6-Trimethyl-benzoyl)diphenylphosphine oxide photochemistry. A direct time-resolved spectroscopic study of both radical fragments" Journal of the American Chemical Society., vol. 117, No. 18, pp. 5148-5153, 1995.
Lindner E. et al.: "Synthese und Stabilisierung von (Benzoyl- und Pentafluorbenzoyloxy)diphenylphosphan und Vergleich mit den entsprechenden isomeren Aroyldiphenylphosphanoxiden", Z. Naturforsch, vol. 36b, pp. 297-300, 1981.
Brierley J. et al.: "The relative apicophilicities pf pseudohalogen substituents in five-coordinate phosphoranes" Phosphorus and Sulfer, vol. 7, pp. 167-169, 1979.
Tani K. et al.: "Acylthio- and thioacyl-thiophosphines ((RCES)nPPh3-n, E=0, S; n=1-3): Synthesis and structural analysis" Bulletin of the Chemical Society of Japan., vol. 73, No. 5, pp. 1243-1252, May 2000.
Sinitsa A.D. et al.: "Phosphorylation of N-substituted carboxamides with phosphorochloridites" Journal of General Chemistry USSR., vol. 56, No. 6, Nov. 20, 1986. XP 002266092.
Burgada R.: "Mécanisme d'acidolyse de la liaison PIII N et d'aminolyse de la liaison PIII OC(O)" Bulletin de la Societe Chimique de France., No. 11, pp. 4161-4163, Nov. 1972. XP 002266093.
Necas M. et al.: "The first six membered genuine heterocycle: (Ph3PCu(Ph2P (S)-N-C(O)Ph))" Phosphorus, Sulfur and Silicon and the Related Elements, vol. 169, pp. 55-58, 2001.
Heinz Bollmacher, Peter Sartori, "Uber Di- Und Tricarboxyphosphine" Chemiker-Zeitung, vol. 107, No. 4, pp. 121-126, 1983.
Heinz Bollmacher, Peter Sartori, "Uber Diphenylcarboxyphosphine" Chemiker-Zeitung, vol. 106, No. 11, pp. 391-395, 1982.
Sartori, Peter: "Uber die Umsetzung von Diphenylchlorphosphin mit Perfluoralkylcarbonsäuren." Zeitung Naturforsch, vol. 31b, pp. 76-80, 1976.
Ullmann's Encyclopedia of Industriaial Chemistry, Kapitel: Liquid-Liquid Extraction-Apparatus, 6th Edition, 2000 Electronic Release.
Friedel-Crafts-Katalysatoren, wie z.B. in George A. Olah, "Friedel-Crafts and Related Reactions", vol. 1, pp. 201, 284-290, 1963.
Nucleophile Katalysatoren, bei Bender in "Mechanismus of Homogeneous Catalysis from Protons to Proteins" Wiley 1971, S. pp. 147-179.
Jerry March: "Advanced Organic Chemistry", 3rd Edition, Wiley, pp. 294, 334 and 347, 1985.
Alok K. Bhattacharya: "The Michaelis-Arbuzov Rearrangement", Chem.Rev., vol. 81, pp. 415-430, 1981.

* cited by examiner

*Primary Examiner*—Rei-tsang Shiao
(74) *Attorney, Agent, or Firm*—Oblon, Spivak, McClelland, Maier & Neustadt, P.C.

(57) ABSTRACT

Process for the preparation of aromatic acylphosphine oxides (II) in which aromatic carboxyphosphines (I) are converted to the acylphosphine oxides (II)

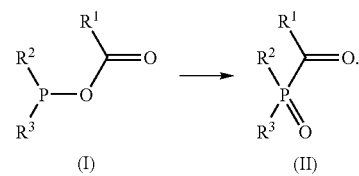

36 Claims, No Drawings

METHOD FOR THE PRODUCTION OF ACYLPHOSPHINE OXIDES

CROSS REFERENCES TO RELATED APPLICATIONS

This application is a national stage application of International Patent Application No. PCT/EP03/10150, filed on Sep. 12, 2003, and claims priority to German Patent Application No. 102 44 684, filed on Sep. 24, 2002, both of which are incorporated herein by reference in their entireties.

The present invention relates to a novel process for the preparation of acylphosphine oxides. This class of substance is used, for example, as photoinitiator or starting material for the synthesis thereof in radiation-curable coating systems.

Monoacylphosphine oxides are known as photoinitiators, for example from EP-A 7508. Bisacylphosphine oxides and their use as photoinitiators are known, for example, from EP-A 184 085.

The synthesis of acylphosphine oxides in an Arbusov rearrangement by reaction of alkoxyphosphines and acid chlorides is known from EP-B 7508:

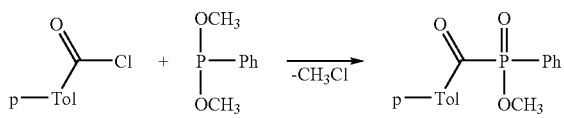

Here, p-Tol=4-methylphenyl and Ph=phenyl.

In this process for the preparation of acylphosphine oxides by reacting carbonyl chlorides with alkoxyphosphines, alkyl chlorides are formed as undesired secondary components in stoichiometric amounts; these necessitate an appropriate disposal expenditure. The carbonyl chloride is obtained from the corresponding carboxylic acid in a complex process by reaction with chlorinating agents, such as thionyl chloride. With the stoichiometric use of an auxiliary base, the alkoxyphosphine is accessible from the corresponding halophosphine. In general, it is still necessary to separate off the neutralized auxiliary base.

U.S. Pat. No. 5,472,992 discloses the synthesis of bisacylphosphines in which a phosphine is diacylated in the presence of a base and then oxidized.

A disadvantage of these synthesis methods, however, is that volatile, toxic and malodorous phosphines have to be used.

In addition, WO 00/32612 discloses the synthesis of acyl- and bisacylphosphines in which an organic phosphoryl halide is brought into contact with an alkali metal or magnesium/lithium and the resulting metallated phosphines are then reacted with an acid chloride:

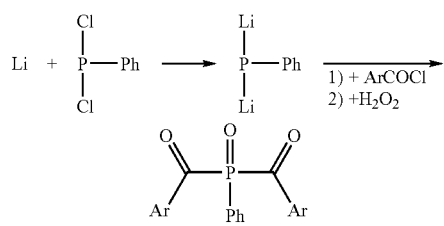

Here, Ph=phenyl and Ar=aryl.

In this process, the chlorophosphines are initially metallated, e.g. by reaction with metallic sodium or lithium, and then reacted with the carbonyl chloride. The acylphosphane then still has to be oxidized to the acylphosphine oxide.

Simpler access to the acylphosphine oxide class of substance would be desirable. In this connection, no alkyl halides should be produced as coproducts which require complex disposal. It would additionally be desirable to use carboxylic acids directly in the synthesis without first having to prepare the corrosive acid chlorides by means of an additional process step. In addition, it would be useful to directly use the chlorophosphines in the synthesis without firstly having to prepare the alkoxyphosphines or metallated phosphides from the chlorophosphines necessary for the Arbusov reaction.

The formation of carboxyphosphines by reaction of the sodium salts of the carboxylic acids with chlorophosphines is described in Chemiker-Zeitung, Volume 107, No. 4, 1983, pages 121-126 (H. Bollmacher, P. Sartori, "Über Di-und Tricarboxyphosphine" [Via di- and tricarboxyphosphines]).

As an alternative to this reaction with sodium salts of the carboxylic acid, the free acid can also be reacted with the chlorophosphines in the presence of stoichiometric amounts of an auxiliary base: Chemiker-Zeitung, Volume 106, No. 11, 1982, pages 391-395 (H. Bollmacher, P. Sartori, "Über Diphenylcarboxyphosphine" [Via diphenylcarboxyphosphines]). Bollmacher and Sartori also report on the reactivity of carboxydiphenylphosphines toward amines, for example diethylamine or pyridine, according to which carboxydiphenylphosphines react to give diphenylphosphinous acid-diethylamide, or decompose into their anhydrides.

J. Brierley, J. I. Dickstein and S. Trippett report, in Phosphorus and Sulfur, Vol. 7, 1979, pages 167-169, on unsuccessful attempts to prepare phosphoranes with 2,4,6-trimethylbenzoyloxy groups (page 168, left-hand column) and describe the preparation of 2,4,6-trimethylbenzoyloxydiphenylphosphine.

From E. Lindner, J. C. Wuhrmann, Z. Naturforsch. 36b, 1981, pages 297-300, it is known that perfluoroacyloxydiphenylphosphanes rearrange at room temperature into the corresponding perfluoroacyldiphenylphosphine oxides, whereas aryloxydiphenylphosphines do not do this and are stable both thermally and also toward nucleophiles.

Only in the case of perfluoroacyloxydiphenylphosphanes could a rearrangement to acylphosphine oxides be observed.

P. Sartori, R. H. Hochleitner and G. Hagele describe, in Z. Naturforsch. 31b, 1976, pages 76-80, on the other hand the reaction of diphenylchlorophosphine with trifluoroacetic acid to give diphenylphosphinic 1-diphenylphosphoryl-2,2,2-trifluoroethyl ester at temperatures up to 170° C.:

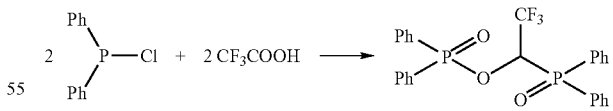

It is an object of the present invention to develop a novel synthesis route for aromatic phosphine oxides in which no stoichiometric amounts of alkyl chlorides are liberated, no complex metallation reactions have to be carried out and the starting materials may be free carboxylic acids or salts thereof.

We have found that this object is achieved by a process for the preparation of aromatic acylphosphine oxides (II) in which aromatic carboxyphosphines (I) are converted to the acylphosphine oxides (II),

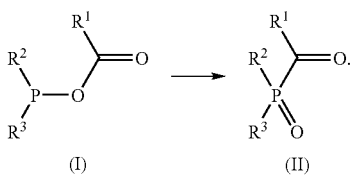

(I) (II)

in which

R¹ is $C_6$-$C_{12}$-aryl or a five- to six-membered aromatic heterocycle having oxygen, nitrogen and/or sulfur atoms, where said radicals can in each case be substituted by aryl, alkyl, aryloxy, alkyloxy, heteroatoms and/or heterocycles, and R² and R³ independently of one another are $C_1$-$C_{18}$-alkyl, $C_1$-$C_{18}$-alkoxy, $C_2$-$C_{18}$-alkyl optionally interrupted by one or more oxygen and/or sulfur atoms and/or one or more substituted or unsubstituted imino groups, $C_2$-$C_{18}$-alkenyl, $C_5$-$C_{12}$-cycloalkyl, $C_6$-$C_{12}$-aryl, $C_1$-$C_{18}$-alkyloyl, $C_6$-$C_{12}$-aryloyl or a five- to six-membered heterocycle having oxygen, nitrogen and/or sulfur atoms, where said radicals can in each case be substituted by aryl, alkyl, aryloxy, alkyloxy, heteroatoms and/or heterocycles, also a metal, a group —O⁻cation⁺ or halogen.

Here, $C_1$-$C_{18}$-alkyl optionally substituted by aryl, alkyl, aryloxy, alkyloxy, heteroatoms and/or heterocycles are, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α, α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxan-2-yl, 1,3-dioxolan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, $C_1$-$C_{18}$-alkoxy optionally substituted by aryl, alkyl, aryloxy, alkyloxy, heteroatoms and/or heterocycles is, for example, methoxy, ethoxy, n-propyloxy, isopropyloxy, n-butyloxy, isobutyloxy, sec-butyloxy, tert-butyloxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 8-methoxy-1,5-dioxooctyl, 12-methoxy-1,5,9-trioxooctyl, 16-methoxy-1,5,9,13-tetraoxohexadecyl, 8-ethoxy-1,5-dioxooctyl, 12-ethoxy-1,5,9-trioxooctyl, 16-ethoxy-1,5,9,13-tetraoxohexadecyl, 10-hydroxy-1,6-dioxodecyl, 15-hydroxy-1,6,11-trioxopentadecyl, 10-methoxy-1,6-dioxodecyl, 15-methoxy-1,6,11-trioxopentadecyl, 10-ethoxy-1,6-dioxodecyl or 15-ethoxy-1,6,11-trioxopentadecyl, $C_2$-$C_{18}$-alkyl optionally interrupted by one or more oxygen and/or sulfur atoms and/or one or more substituted or unsubstituted imino groups is, for example, 5-hydroxy-3-oxa-pentyl, 8-hydroxy-3,6-dioxa-octyl, 11-hydroxy-3,6,9-trioxa-undecyl, 7-hydroxy-4-oxa-heptyl, 11-hydroxy-4,8-dioxa-undecyl, 15-hydroxy-4,8,12-trioxa-pentadecyl, 9-hydroxy-5-oxa-nonyl, 14-hydroxy-5,10-oxa-tetradecyl, 5-methoxy-3-oxa-pentyl, 8-methoxy-3,6-dioxa-octyl, 11-methoxy-3,6,9-trioxa-undecyl, 7-methoxy-4-oxa-heptyl, 11-methoxy-4,8-dioxa-undecyl, 15-methoxy-4,8,12-trioxa-pentadecyl, 9-methoxy-5-oxa-nonyl, 14-methoxy-5,10-oxa-tetradecyl, 5-ethoxy-3-oxa-pentyl, 8-ethoxy-3,6-dioxa-octyl, 11-ethoxy-3,6,9-trioxa-undecyl, 7-ethoxy-4-oxa-heptyl, 11-ethoxy-4,8-dioxa-undecyl, 15-ethoxy-4,8,12-trioxa-pentadecyl, 9-ethoxy-5-oxa-nonyl or 14-ethoxy-5,10-oxa-tetradecyl.

The number of oxygen and/or sulfur atoms and/or imino groups is not limited. It usually is not more than 5 in the radical, preferably not more than 4 and very particularly preferably not more than 3.

In addition, there is usually one carbon atom, preferably at least two, between two heteroatoms.

Substituted and unsubstituted imino groups can, for example, be imino, methylimino, isopropylimino, n-butylimino or tert-butylimino.

In addition $C_2$-$C_{18}$-alkenyl optionally substituted by aryl, alkyl, aryloxy, alkyloxy, heteroatoms and/or heterocycles is, for example, vinyl, 1-propenyl, allyl, methallyl, 1,1-dimethylallyl, 2-butenyl, 2-hexenyl, octenyl, undecenyl, dodecenyl, octadecenyl, 2-phenylvinyl, 2-methoxyvinyl, 2-ethoxyvinyl, 2-methoxyallyl, 3-methoxyallyl, 2-ethoxyallyl, 3-ethoxyallyl or 1- or 2-chlorovinyl, $C_6$-$C_{12}$-aryl optionally substituted by aryl, alkyl, aryloxy, alkyloxy, heteroatoms and/or heterocycles is, for example, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl optionally substituted by aryl, alkyl, aryloxy, alkyloxy, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, and a saturated or unsaturated bicyclic system, such as, for example, norbornyl or norbornenyl, a five- to six-membered heterocycle having oxygen, nitrogen, and/or sulfur atoms is, for example, furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl, a $C_1$-$C_{18}$-alkyloyl optionally substituted by aryl, alkyl, aryloxy, alkyloxy, heteroatoms and/or heterocycles is acetyl, propionyl, n-butyryl, isobutyryl, sec-butyryl, tert-butyryl, stearyl, trifluoroacetyl, chloroacetyl, dichloroacetyl, trichloroacetyl, pentafluoropropionyl or phenylacetyl, a $C_6$-$C_{12}$-aryloyl optionally substituted by aryl, alkyl, aryloxy, alkyloxy, heteroatoms and/or heterocycles is benzoyl, 2-, 3- or 4-($C_1$-$C_4$-alkyl)benzoyl, 2-, 3- or 4-chlorobenzoyl, 2-, 3- or 4-($C_1$-$C_4$-alkyloxy)benzoyl, 2,3-, 2,4-, 2,5- or 2,6-di($C_1$-$C_4$-alkyl)benzoyl, 2,3-, 2,4-, 2,5- or 2,6-dichlorobenzoyl, 2,3-, 2,4-, 2,5- or 2,6-di($C_1$-$C_4$-alkyloxy)benzoyl, 2,3,4-, 2,3,5-, 2,3,6-, 2,4,5- or 2,4,6-tri($C_1$-$C_4$-alkyl)benzoyl, 2,3,4-, 2,3,5-, 2,3,6-, 2,4,5- or 2,4,6-trichlorobenzoyl or 2,3,4-, 2,3,5-, 2,3,6-, 2,4,5- or 2, 4, 6-tri ($C_1$-$C_4$-alkyloxy) benzoyl, a metal is, for example, an equivalent of a metal chosen from the group consisting of Li, Na, K, Cs, Be, Mg, Ca, Ba, Ti, Zr, Cr, Mo, Fe, Co, Ni, Cu, Zn, Al or Sn and halogen is, for example, F, Cl, Br or I.

In addition, in a group —O⁻ cation⁺, the term cation⁺ is an equivalent of a cation of the metals listed above or of an ammonium ion, as are listed, for example, in EP-Al 62 839, p. 3, 1. 26 to p. 4, 1. 3 with the meanings defined therein for the radicals $R^5$ to $R^9$.

The number of substituents in the given radicals is not limited. For radicals with one to three carbon atoms it is usually up to 3 substituents, preferably up to 2 and particularly preferably up to one. For the radicals with four to six carbon atoms, it is usually up to 4 substituents, preferably up to 3 and particularly preferably up to one. For radicals with more than seven carbon atoms, it is usually up to 6 substituents, preferably up to 4 and particularly preferably up to two.

Within the scope of this specification, $C_1$-$C_4$-alkyl is methyl, ethyl, n-propyl, isopropyl, n-butyl, isobutyl, sec-butyl or tert-butyl, if not mentioned otherwise preferably methyl or ethyl and particularly preferably methyl.

$R^1$ is preferably phenyl, tolyl, xylyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-isopropylphenyl, 2-, 0.3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, 2- or 3-furyl, 2- or 3-thiophenyl, 2- or 3-pyrryl or dimethylpyrryl.

$R^1$ is particularly preferably phenyl, tolyl, α-naphthyl, β-naphthyl, 2,6- or 2,4-dichlorophenyl, 2,4,6-trichlorophenyl, 2,6- or 2,4-dimethylphenyl, 2,4,6-trimethylphenyl, 2,6- or 2,4-diethylphenyl, 2-isopropylphenyl, 2-tert-butylphenyl, 2,6- or 2,4-dimethoxyphenyl, 2,6- or 2,4-diethoxyphenyl, methylnaphthyl, 2,4,6-trimethoxyphenyl, 2,6-dimethoxyphenyl, 2,6-dichlorophenyl, 2,6-dinitrophenyl or ortho-substituted phenyls, such as 2-methylphenyl, 2-methoxyphenyl or 2-chlorophenyl.

$R^1$ is very particularly preferably phenyl, 2-methylphenyl, 2-methoxyphenyl, 2-chlorophenyl, α-naphthyl, 2,6-dichlorophenyl, 2,4,6-trichlorophenyl, 2,6-dimethylphenyl, 2,4,6-trimethylphenyl, 2,6-diethylphenyl, 2,6-dimethoxyphenyl, 2,6-diethoxyphenyl, 2,6-dimethoxyphenyl, 2,4,6-trimethoxyphenyl, 2,6-dimethoxyphenyl, 2,6-dichlorophenyl or 2,6-dinitrophenyl.

$R^1$ is in particular 2,6-dichlorophenyl, 2,4,6-trichlorophenyl, 2,6-dimethylphenyl, 2,4,6-trimethylphenyl, 2,4,6-trimethoxyphenyl or 2,6-dimethoxyphenyl and specifically 2,4,6-trimethylphenyl.

$R^2$ and $R^3$ independently of one another are preferably 2,4,4-trimethylpentyl, benzyl, p-chlorobenzyl, 2,4-dichlorobenzyl, p-methoxybenzyl, methoxy, ethoxy, n-propyloxy, isopropyloxy, n-butyloxy, isobutyloxy, sec-butyloxy, tert-butyloxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5, 9-trioxooctyl, 16-hydroxy-1,5,9,13-tetraoxohexadecyl, 10-hydroxy-1,6-dioxodecyl, 15-hydroxy-1,6,11-trioxopentadecyl, vinyl, 1-propenyl, allyl, methallyl, 1,1-dimethylallyl, 2-butenyl, 2-hexenyl, 2-phenylvinyl, 2-methoxyvinyl, 2-ethoxyvinyl, 2-chlorovinyl, phenyl, tolyl, xylyl, α-naphthyl, β-naphthyl, 4-diphenylyl, 2-, 3- or 4-chlorophenyl, 2,4- or 2,6-dichlorophenyl, 2,4,6-trichlorophenyl, 2-, 3- or 4-methylphenyl, 2,4- or 2,6-dimethylphenyl, 2,4,6-trimethylphenyl, 2-, 3- or 4-ethylphenyl, 2,4- or 2,6-diethylphenyl, 2-, 3- or 4-isopropylphenyl, 2-, 3- or 4-tert-butylphenyl, 2-, 3- or 4-methoxyphenyl, 2,4- or 2,6-dimethoxyphenyl, 2-, 3- or 4-ethoxyphenyl, methylnaphthyl, chloronaphthyl, ethoxynaphthyl, 2,6-dimethylphenyl, 2,4,6-trimethylphenyl, 2,4- or 2,6-dimethoxyphenyl, 2,4- or 2,6-dichlorophenyl, 2- or 4-nitrophenyl, 2,4- or 2,6-dinitrophenyl, 4-dimethylaminophenyl, 4-acetylphenyl, 2,4,6-trimethylbenzoyl, 2,6-dimethoxybenzoyl or 2,6-dichlorobenzoyl.

$R^2$ and $R^3$ independently of one another are particularly preferably benzyl, p-chlorobenzyl, 2,4-dichlorobenzyl, p-methoxybenzyl, methoxy, ethoxy, n-propyloxy, isopropyloxy, n-butyloxy, isobutyloxy, sec-butyloxy, tert-butyloxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7, 10-tetraoxododecyl, 6-ethoxy-1,4-dioxohexyl, 9-ethoxy-1, 4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, vinyl, 2-butenyl, 2-phenylvinyl, phenyl, tolyl, xylyl, α-naphthyl, β-naphthyl, 4-diphenylyl, 2-, 3- or 4-chlorophenyl, 2,4- or 2,6-dichlorophenyl, 2,4,6-trichlorophenyl, 2-, 3- or 4-methylphenyl, 2,4- or 2,6-dimethylphenyl, 2,4,6-trimethylphenyl, 2-, 3- or 4-ethylphenyl, 2-, 3- or 4-isopropylphenyl, 2-, 3- or 4-tert-butylphenyl, 2-, 3- or 4-methoxyphenyl, 2,4- or 2,6-dimethoxyphenyl, 2-, 3- or 4-ethoxyphenyl, methylnaphthyl, chloronaphthyl, ethoxynaphthyl, 2- or 4-nitrophenyl, 2,4- or 2,6-dinitrophenyl, 4-dimethylaminophenyl, 4-acetylphenyl, 2,4,6-trimethylbenzoyl, 2,6-dimethoxybenzoyl or 2,6-dichlorobenzoyl.

$R^2$ and $R^3$ independently of one another are very particularly preferably methoxy, ethoxy, n-propoxy, isopropoxy, n-butyloxy, sec-butyloxy, isobutyloxy, tert-butyloxy, phenyl, xylyl, α-naphthyl, β-naphthyl, 4-diphenylyl, 2-, 3- or 4-chlorophenyl, 2,4-dichlorophenyl, 2-, 3- or 4-methylphenyl, 2,4-dimethylphenyl, 2-, 3- or 4-ethylphenyl, 2-, 3- or 4-methoxyphenyl, 2,4-dimethoxyphenyl, 2-, 3- or 4-ethoxyphenyl, methylnaphthyl, chloronaphthyl, ethoxynaphthyl, 2- or 4-nitrophenyl, 2,4,6-trimethylbenzoyl, 2,6-dimethoxybenzoyl or 2,6-dichlorobenzoyl.

$R^2$ and $R^3$-independently of one another are in particular methoxy, ethoxy, n-propoxy, isopropoxy, n-butyloxy, sec-butyloxy, isobutyloxy, tert-butyloxy, phenyl, 4-diphenylyl, 2-, 3- or 4-chlorophenyl, 2-, 3- or 4-methylphenyl, 2-, 3- or 4-methoxyphenyl, 2-, 3- or 4-ethoxyphenyl, 2,4,6-trimethylbenzoyl, 2,6-dimethoxybenzoyl or 2,6-dichlorobenzoyl.

$R^2$ and $R^3$ independently of one another are specifically phenyl or 4-methylphenyl.

This invention further provides aromatic carboxyphosphines (Ia), in which the radicals $R^1$, $R^2$ and $R^3$ given in formula (I) have the following meanings:

$R^1$ is preferably phenyl, tolyl, xylyl, α-naphthyl, β-naphthyl, 2-3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-isopropylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, 2- or 3-furyl, 2- or 3-thiophenyl, 2- or 3-pyrryl or dimethylpyrryl.

$R^1$ is particularly preferably phenyl, tolyl, α-naphthyl, β-naphthyl, 2,6- or 2,4-dichlorophenyl, 2,4,6-trichlorophenyl, 2,6- or 2,4-dimethylphenyl, 2,4,6-trimethylphenyl, 2,6- or 2,4-diethylphenyl, 2-isopropylphenyl, 2-tert-butylphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 2,6-dinitrophenyl or ortho-substituted phenyls, 2-methylphenyl, 2-methoxyphenyl or 2-chlorophenyl.

$R^1$ is very particularly preferably phenyl, 2-methylphenyl, 2-methoxyphenyl, 2-chlorophenyl, α-naphthyl, 2,6-dichlorophenyl, 2,4,6-trichlorophenyl, 2,6-dimethylphenyl, 2,4,6-trimethylphenyl, 2,6-diethylphenyl, 2,6-dimethoxyphenyl, 2,6-diethoxyphenyl, 2,6-dimethylphenyl, 2,4,6-trimethylphenyl, 2,6-dimethoxyphenyl, 2,6-dichlorophenyl or 2,6-dinitrophenyl.

$R^1$ is in particular phenyl, 2,6-dichlorophenyl, 2,4,6-trichlorophenyl, 2,6-dimethylphenyl, 2,4,6-trimethylphenyl or 2,6-dimethoxyphenyl.

$R^2$ and $R^3$ independently of one another can assume the meanings listed above.

$R^2$ and $R^3$ independently of one another are preferably 2,4,4-trimethylpentyl, benzyl, p-chlorobenzyl, 2,4-dichlorobenzyl, p-methoxybenzyl, methoxy, ethoxy, n-propyloxy, isopropyloxy, n-butyloxy, isobutyloxy, sec-butyloxy, tert-butyloxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, vinyl, 1-propenyl, allyl, methallyl, 1,1-dimethylallyl, 2-butenyl, 2-hexenyl, 2-phenylvinyl, 2-methoxyvinyl, 2-ethoxyvinyl, 2-chlorovinyl, phenyl, tolyl, xylyl, α-naphthyl, β-naphthyl, 4-diphenylyl, 2-, 3- or 4-chlorophenyl, 2,4- or 2,6-dichlorophenyl, 2,4,6-trichlorophenyl, 2-, 3- or 4-methylphenyl, 2,4- or 2,6-dimethylphenyl, 2,4,6-trimethylphenyl, 2-, 3- or 4-ethylphenyl, 2,4- or 2,6-diethylphenyl, 2-, 3- or 4-isopropylphenyl, 2-, 3- or 4-tert-butylphenyl, 2-, 3- or 4-methoxyphenyl, 2,4- or 2,6-dimethoxyphenyl, 2-, 3- or 4-ethoxyphenyl, methylnaphthyl, chloronaphthyl, ethoxynaphthyl, 2,6-dimethylphenyl, 2,4,6-trimethylphenyl, 2,4- or 2,6-dimethoxyphenyl, 2,4- or 2,6-dichlorophenyl, 2- or 4-nitrophenyl, 2,4- or 2,6-dinitrophenyl, 4-dimethylaminophenyl, 4-acetylphenyl, 2,4,6-trimethylbenzoyl or chloro.

$R^2$ and $R^3$ independently of one another are particularly preferably benzyl, p-chlorobenzyl, 2,4-dichlorobenzyl, p-methoxybenzyl, methoxy, ethoxy, n-propyloxy, isopropyloxy, n-butyloxy, isobutyloxy, sec-butyloxy, tert-butyloxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, vinyl, 2-butenyl, 2-phenylvinyl, phenyl, tolyl, xylyl, α-naphthyl, β-naphthyl, 4-diphenylyl, 2-, 3- or 4-chlorophenyl, 2,4- or 2,6-dichlorophenyl, 2,4.,6-trichlorophenyl, 2-, 3- or 4-methylphenyl, 2,4- or 2,6-dimethylphenyl, 2,4,6-trimethylphenyl, 2-, 3- or 4-ethylphenyl, 2-, 3- or 4-isopropylphenyl, 2-, 3- or 4-tert-butylphenyl, 2-, 3- or 4-methoxyphenyl, 2,4- or 2,6-dimethoxyphenyl, 2-, 3- or 4-ethoxyphenyl, methylnaphthyl, chloronaphthyl, ethoxynaphthyl, 2- or 4-nitrophenyl, 2,4- or 2,6-dinitrophenyl, 4-dimethylaminophenyl, 4-acetylphenyl, 2,4,6-trimethylbenzoyl or chloro.

$R^2$ and $R^3$ independently of one another are very particularly preferably methoxy, ethoxy, n-propoxy, isopropoxy, n-butyloxy, sec-butyloxy, isobutyloxy, tert-butyloxy, 6-hydroxy-1,4-dioxohexyl, 9-hydroxy-1,4,7-trioxononyl, 12-hydroxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, phenyl, xylyl, α-naphthyl, β-naphthyl, 4-diphenylyl, 2-, 3- or 4-chlorophenyl, 2,4-dichlorophenyl, 2-, 3- or 4-methylphenyl, 2,4-dimethylphenyl, 2-, 3- or 4-ethylphenyl, 2-, 3- or 4-methoxyphenyl, 2,4-dimethoxyphenyl, 2-, 3- or 4-ethoxyphenyl, methylnaphthyl, chloronaphthyl, ethoxynaphthyl, 2- or 4-nitrophenyl, 2,4,6-trimethylbenzoyl or chloro.

$R^2$ and $R^3$ independently or one another are in particular methoxy, ethoxy, n-propoxy, isopropoxy, n-butyloxy, sec-butyloxy, isobutyloxy, tert-butyloxy, phenyl, 4-diphenylyl, 2-, 3- or 4-chlorophenyl, 2-, 3- or 4-methylphenyl, 2-, 3- or 4-methoxyphenyl, 2-, 3- or 4-ethoxyphenyl or 2,4,6-trimethylbenzoyl.

$R^2$ and $R^3$ independently of one another are specifically phenyl, 4-methylphenyl or 2,4,6-trimethylbenzoyl.

$R^2$ and $R^3$ may be identical or different, they are preferably identical except when one of the radicals $R^2$ and $R^3$ is 2,4,6-trimethylbenzoyl, in this case the other is preferably phenyl.

Very particular preference is given to the following carboxyphosphines in which $R^1$ is chosen from the aromatic radicals listed above which are substituted in at least one ortho position relative to the carbonyl group by a radical other than hydrogen and $R^2$ and $R^3$ independently of one another are chosen from the group consisting of methoxy, ethoxy, n-propyloxy, isopropyloxy, n-butyloxy, isobutyloxy, sec-butyloxy, tert-butyloxy, phenyl, 4-methylphenyl, 4-chlorophenyl, 4-methoxyphenyl, 2,4,4-trimethylpentyl, 2,6-dimethoxybenzoyl and 2,4,6-trimethylbenzoyl.

Very particular preference is given to those carboxyphosphines (Ia) specified in which $R^1$ is chosen from the group consisting of 2,4,6-trimethylphenyl, 2,6-dimethylphenyl, 2,6-dichlorophenyl, 2,6-dimethoxyphenyl, 2-methylphenyl, 2-chlorophenyl and 2-methoxyphenyl and $R^2$ and $R^3$ independently of one another are chosen from the group consisting of methoxy, ethoxy, n-propyloxy, isopropyloxy, n-butyloxy, isobutyloxy, sec-butyloxy, tert-butyloxy, phenyl, 4-methylphenyl, 4-chlorophenyl, 4-methoxyphenyl, 2,4,4-trimethylpentyl, 2,6-dimethoxybenzoyl and 2,4,6-trimethylbenzoyl.

Specific preference is given to those carboxyphosphines (Ia) mentioned in which $R^2$ and $R^3$ are identical.

These carboxyphosphines (Ia) represent valuable intermediates in the synthesis of the corresponding acylphosphines by the process according to the invention.

The synthesis of carboxyphosphines (I) is known from the prior art, for example from the literature references cited at the beginning.

According to the prior art, for example, the sodium salt of the carboxylic acid is reacted in diethyl ether at low temperatures (0° C.) with a chlorophosphine, with NaCl precipitating out and the carboxyphosphine remaining in solution. The precipitated NaCl is filtered off. If the solvent is removed, the carboxyphosphine is left behind as an oil or solid.

Instead of the sodium salt of the carboxylic acid it is also possible to react the free carboxylic acid in the presence of a tertiary amine, in which case, according to H. Bollmacher, P. Sartori, Chemiker-Zeitung, Volume 106, No. 11, 1982, page 392, the carboxyphosphines are partially decomposed into the anhydrides by the auxiliary base, which leads to poor yields in this synthesis method. The preparation methods described in the literature are complex, particularly since the salt of the auxiliary base is produced as a solid and since the reaction has to be carried out at low temperatures.

Carboxyphosphines are obtainable according to the invention, for example, according to the following reaction equation:

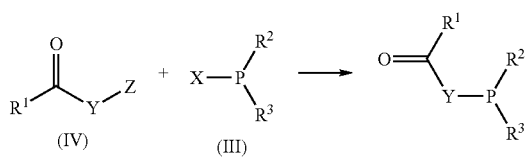

Here, $R^1$, $R^2$ and $R^3$ have the meanings listed above.

In addition,

X is halogen, pseudohalogen, un-, mono- or disubstituted nitrogen or sulfuryloxy, preferably halogen, Y is oxygen, sulfur, un- or monosubstituted nitrogen, preferably oxygen and Z is hydrogen, or an equivalent of a cation.

Here, halogen is, for example, F, Cl, Br or I, preferably Cl, pseudohalogen is, for example, CN, OCN or SCN, un-, mono- or disubstituted nitrogen is $-NH_2$, $-NHR^2$ or $-NR^2R^3$ or $-NH-$ or $-NR^2-$, where $R^2$ and $R^3$ have the same meanings as listed above, but may be different from $R^2$ and $R^3$ in the compound (III), preferably it is a nitrogen atom mono-, di- or trisubstituted by hydrogen or $C_1$-$C_4$-alkyl, and sulfuryloxy is, for example, tosylate, brosylate, mesylate or triflate.

In this regard, cations can be as defined above or additionally protonated auxiliary bases (see below), preferably protonated auxiliary bases, $Na^+$, $K^+$, $Li^+$, $Cs^+$, $Mg^{2+}$, $Ca^{2+}$, $Al^{3+}$, or primary, secondary, tertiary or quaternary ammonium substituted by $C_1$-$C_4$-alkyl and particularly preferably protonated auxiliary bases.

The reaction of components (IV) and (III) with one another can take place according to the invention without a diluent or in the form of a dispersion or solution in a suitable solvent at a temperature between, for example, −20° C. and 160° C., preferably between 0 and 140° C., particularly preferably between 50 and 120° C. and in particular between 60 and 100° C., preferably in the presence of an auxiliary base.

The reaction time is generally from a few minutes to a few hours, preferably 10 minutes to 10 hours, particularly preferably 10 to 300 minutes, very particularly preferably 30 to 200 minutes.

In a preferred embodiment, the conversion of components (IV) and (III) to carboxyphosphines can be coupled with the rearrangement of the resulting carboxyphosphines to give acylphosphine oxides by reacting the components (IV) and (III) with one another at temperatures up to 240° C. without isolation of any resulting intermediates. The reaction temperature can remain constant during such a reaction or be increased over the course of the reaction.

Suitable auxiliary bases are those which, protonated as a salt, with the anionic compounds of (IV), form $R^1(CO)Y^-$, or, with $X^-$, form a salt with a melting point below 160° C., particularly preferably below 100° C. and very particularly preferably below 80° C.

Preferred auxiliary bases are those as listed in German patent application dated 24.01.2002 with the file reference 10202838.9, particularly those listed in the filed text on p. 6, l. 37 to p. 14, l 42.

Particular preference is given to 3-chloropyridine, 4-dimethylaminopyridine, 2-ethyl-4-aminopyridine, 2-methylpyridine (α-picoline), 3-methylpyridine (β-picoline), 4-methylpyridine (γ-picoline), 2-ethylpyridine, 2-ethyl-6-methylpyridine, quinoline, isoquinoline, pyridine, 1-$C_1$-$C_4$-alkylimidazole, 1-methylimidazole, 1,2-dimethylimidazole, 1-n-butylimidazole, 1,4,5-trimethylimidazole, 1,4-dimethylimidazole, imidazole, 2-methylimidazole, 1-butyl-2-methylimidazole, 4-methylimidazole, 1-n-pentylimidazole, 1-n-hexylimidazole, 1-n-octylimidazole, 1-(2'-aminoethyl)imidazole, 2-ethyl-4-methylimidazole, 1-vinylimidazole, 2-ethylimidazole, 1-(2'-cyanoethyl)imidazole and benzotriazole.

Very particular preference is given to 1-n-butylimidazole, 1-methylimidazole, 2-methylpyridine and 2-ethylpyridine, special preference being given to 1-methylimidazole.

The solvents used may, for example, be benzene, toluene, o-, m- or p-xylene, cyclohexane, cyclopentane, pentane, hexane, heptane, octane, petroleum ether, acetone, isobutyl methyl ketone, diethyl ketone, diethyl ether, tert-butyl methyl ether, tert-butyl ethyl ether, tetrahydrofuran, dioxane, acetic ester, methyl acetate, dimethylformamide, dimethyl sulfoxide, acetonitrile or mixtures thereof. Preference is given to using a solvent which is immiscible with the salt of the auxiliary base listed above.

If no auxiliary base which forms a liquid salt is used in the synthesis, then the carboxyphosphine (I) is removed from the reaction mixture as described in the prior art, for example by filtration, crystallization, extraction, distillation or rectification.

If, on the other hand, a liquid salt has been formed in the reaction, this is preferably separated off by means of a liquid-liquid phase separation at a temperature above the melting point of the liquid salt, preferably 5 to 30° C. above the melting point, for example in a phase separator or a mixer-settler apparatus.

Surprisingly, it has been found that the decomposition, known from the literature, of the product into the anhydrides is not observed in the inventive presence of an auxiliary base.

The carboxyphosphine can then, if desired, be further purified, for example by washing or recrystallization. As a rule, purities of 80% by weight or more, preferably 90% or more, particularly preferably 95% or more and very particularly preferably 98% or more, are adequate.

The described process is advantageously suitable for the preparation of carboxyphosphines of the formula (Ia).

The carboxyphosphine can then be converted according to the invention to the acylphosphine oxide (II).

The rearrangement to the acylphosphine oxide (II) can take place thermally and/or catalytically.

The rearrangement can either be carried out thermally without a diluent or in the form of a solution or dispersion in solvents, for example those given above, preferably the polar solvents, above 100° C., preferably above 120° C., particularly preferably above 140° C. and very particularly preferably above 160° C.

If a catalyst is added, the rearrangement takes place more quickly and at lower temperatures, for example above 80° C., preferably above 100° C. and very particularly preferably above 120° C.

The reaction time can be from a few minutes to a few hours, for example 5 minutes to 5 hours, preferably 10 minutes to 3 hours and particularly preferably 15 minutes to 2 hours.

The formation of carboxyphosphine and the rearrangement can be carried out discontinuously, semicontinuously or continuously in two separate reactors or else as a one-pot synthesis.

The reaction can advantageously be carried out in the presence of a gas which is inert under the reaction conditions, for example nitrogen, air, nitrogen-oxygen mixtures, argon, helium, carbon dioxide or monoxide, preferably nitrogen or argon.

The pressure at which the reaction according to the invention is carried out is not decisive, the reaction can be carried out at subatmospheric pressure, superatmospheric pressure or atmospheric pressure, preferably at atmospheric pressure or superatmospheric pressure up to, for example, 5 bar in order to remain below the boiling point of the optionally used solvent.

It is possible to carry out the reaction only up to a partial conversion, for example up to 75%, preferably up to 50%, particularly preferably up to 30% and very particularly preferably up to 20%, to separate starting material and product and to return the starting material to the reaction. The starting material and product can be separated, for example, as described above, preferably by distillation, fractional crystallization or by liquid-liquid extraction.

A liquid-liquid extraction can take place, for example, by separating at least part of the completely or partially reacted reaction mixture in a mixture of at least two immiscible solvents of varying polarity.

In terms of processing technology, all extraction processes and apparatuses known per se can in principle be used for this purpose, e.g. those described in Ullmann's Encyclopedia of Industrial Chemistry, 6th ed, 1999 Electronic Release, Chapter: Liquid-Liquid Extraction—Apparatus. For example, these may be single-stage or multistage, preferably multistage, extractions, and those in cocurrent or countercurrent operation, preferably countercurrent operation.

Preference is given to using perforated-plate columns, columns with dumped or arranged packings, stirred containers or mixer-settler apparatuses and also columns with rotating internals or pulsed columns.

Solvents of relatively high polarity are, for example, alcohols, such as, for example, methanol, ethanol, isopropanol, n-propanol, n-butanol, isobutanol, sec-butanol, tert-butanol, ketones, such as, for example, acetone, isobutyl methyl ketone, diethyl ketone, ethers, such as, for example, diethyl ether, isobutyl methyl ether, isobutyl ethyl ether, dioxane, tetrahydrofuran, dimethylformamide, dimethylacetamide, dimethyl sulfoxide, sulfolane, ethylene carbonate, propylene carbonate or tetrabutylurea.

Solvents of relatively low polarity are, for example cycloaliphatic or aliphatic hydrocarbons such as, for example, n-pentane, n-hexane, n-heptane, petroleum ether mixtures, light benzines, cyclohexane, methylcyclohexane or cyclopentane, aromatic hydrocarbons, such as, for example, benzene, toluene or xylene isomer mixtures or halogenated hydrocarbons, such as, for example, carbon tetrachloride, chloroform, methylchloroform or methylene chloride.

The concentration of the reaction product (acylphosphine oxide) usually increases in the polar phase.

Preferred solvent systems are sulfolane/tetrabutylurea, sulfolane/hexane and methanol/n-heptane.

The catalyst can be used in substoichiometric, stoichiometric or superstoichiometric amounts, preferably in amounts of from 5 to 100 mol %, based on the starting material, particularly preferably in amounts of from 5 to 50 and very particularly preferably 10 to 30 mol %.

Suitable catalysts are, for example,

Friedel-Crafts catalysts, as described, for example, in George A. Olah, "Friedel-Crafts and Related Reactions", Vol. I, 201 and 284-290 (1963).

Lewis-acidic ionic liquids

Nucleophilic catalysts as are described, for example, by Bender in "Mechanism of Homogeneous Catalysis from Protons to Proteins", Wiley 1971, pp. 147-179 or in Jerry March "Advanced Organic Chemistry", 3rd ed. Wiley, 1985, p. 294 f., p. 334, 347.

Acid chlorides, preferably the acid chloride of the carboxylic acid used

Acid anhydrides, preferably the acid anhydride of the carboxylic acid or trifluoroacetic anhydride used.

Alkyl halides

Halogens

Arbusov catalysts, as are described, for example, in Alok, K. Bhattacharya and G. Thyagarajan, Chem. Rev. 1981, 81, 415-430.

Photons (light quanta)

Catalysts with simultaneous Lewis-acidic and Lewis-basic properties, such as, for example, trimethylsilyl cyanide or LiI Heterogeneous catalysts with Lewis-acidic properties Transition metals with high affinity to phosphorus, such as, for example, Fe(CO)$_5$ Preference is given to aluminum trichloride (AlCl$_3$), iron (III) chloride (FeCl$_3$), aluminum tribromide (AlBr$_3$), zinc chloride (ZnCl$_2$), trifluoroacetic anhydride, the acid chloride R$^1$COCl or acid anhydride (R$^1$CO)$_2$O of the compound (IV) used, KI, NaI, LiI or trimethylsilyl cyanide, and particular preference is given to AlCl$_3$, trifluoroacetic anhydride, R$^1$COCl, (R$^1$CO)$_2$O or KI.

Surprisingly, it has been found that the rearrangement according to the invention can also be carried out with non-perfluorinated acyloxyphosphanes.

In addition, it is surprising that the decomposition of carboxyphosphines reported by Bollmacher and Sartori does not take place in the presence of amines in the process according to the invention.

The acylphosphine oxides obtainable according to the invention can be used, for example, as photoinitiators in radiation curing.

Unless stated otherwise, ppm and percentages used in this specification refer to percentages and ppm by weight.

EXAMPLES

Example 1

Preparation of trimethylbenzoyloxydiphenylphosphine (TBOP)

43.1 g of 1-methylimidazole, 300 ml of di-n-butyl ether and 82.1 g of trimethylbenzoic acid were combined in a glass flask rinsed inert with nitrogen. Then, at 80° C. and with stirring, 110.3 g of diphenylchlorophosphine were added dropwise to the reaction mixture over the course of 62 min, during which the mixture initially became cloudy and a little later two liquid phases formed. The mixture was stirred for a further 3 hours at 80° C. and phase separation was carried out at 80° C.

The upper phase was cooled, during which 151.8 g of TBOP precipitated out in the form of colorless crystals. The TBOP was filtered off and dried at 70° C. under reduced pressure. The yield was 87%.

Example 2

Rearrangement of trimethylbenzoyloxydiphenylphosphine in trimethylbenzoyldiphenylphosphine oxide (TPO)

5 g of TBOP were initially introduced into a glass flask rendered inert with argon, and heated. At about 80° C. the TBOP melted. After 45 min at 220° C. the reaction mixture was intense yellow in color.

The TPO was formed as a yellow oil and was characterized by means of IR, UV, $^{31}$P-NMR.

Example 3

5 g of TBOP were initially introduced into a glass flask rendered inert with argon, and heated to 180° C. After 253 min, a sample was taken and investigated by means of $^{31}$P-NMR. The conversion of TBOP was 93.9% according to $^{31}$P-NMR.

Example 4

5 g of TBOP and 0.26 g of trimethylbenzoyl chloride (TMBC) were initially introduced into a glass flask rendered inert with argon, and heated to 158° C., during which the mixture became intense yellow in color. After 170 min, a sample was analyzed. The TPO was produced as a yellow oil.

Example 5

5 g of TBOP and 0.2 g of AlCl$_3$ were initially introduced into a glass flask rendered inert with argon, and heated to 180° C., during which the mixture became intense yellow in color. The TPO was produced after 36 min as a yellow oil.

Example 6

5 g of TBOP and 0.2 g of potassium iodide were initially introduced into a glass flask rendered inert with argon, and heated to 180° C., during which the mixture became intense yellow in color. The TPO was produced after 39 min as a yellow oil.

Example 7

5 g of TBOP and 0.2 g of potassium iodide were initially introduced with 10 mol % of trifluoroacetic anhydride in dimethylacetamide into a glass flask rendered inert with argon, and heated to 165° C., during which the mixture became intense yellow in color. The TPO was produced after 15 min as a yellow oil.

We claim:

1. A process for preparing an aromatic acylphosphine oxide (II), wherein said process comprises converting an aromatic carboxyphosphine (I) to said aromatic acylphosphine oxide (II) according to the following rearrangement reaction:

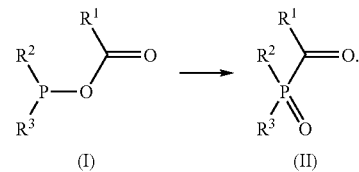

wherein R$^1$ is a C$_6$-C$_{12}$ aryl group, which is optionally substituted by at least one aryl, alkyl, aryloxy, alkyloxy, and/or heteroatom, and wherein R$^2$ and R$^3$ each independently represent a C$_1$-C$_{18}$ alkyl group, a C$_2$-C$_{18}$ alkyl group optionally interrupted by one or more oxygen atoms, sulfur atoms and/or substituted or unsubstituted imino groups, a C$_2$-C$_{18}$-alkenyl group, a C$_6$-C$_{12}$-aryl group, a C$_5$-C$_{12}$-cycloalkyl group, or a C$_1$-C$_{18}$-alkoxy group, which are optionally substituted by at least one aryl, alkyl, aryloxy, alkyloxy, heteroatom, metal, —O$^-$cation$^+$and/or halogen.

2. The process for preparing an aromatic acylphosphine oxide (II) according to claim 1, wherein R$^1$ is selected from the group consisting of phenyl, tolyl, xylyl, α-naphthyl, β-naphthyl, 2-chlorophenyl, 3-chlorophenyl, 4-chlorophenyl, 2,6-dichlorophenyl, 2,4-dichlorophenyl, 2,4,6-trichlorophenyl, 2-methylphenyl, 3-methylphenyl, 4-methylphenyl, 2,6-dimethylphenyl, 2,4-dimethylphenyl, 2,4,6- trimethylphenyl, 2-ethylphenyl, 3-ethylphenyl, 4-ethylphenyl, 2,6-diethylphenyl, 2,4-diethylphenyl, 2-isopropylphenyl, 3-isopropylphenyl, 4-isopropylphenyl, 2-tert-butylphenyl, 3-tert-butylphenyl, 4-tert-butylphenyl, 2-methoxyphenyl, 3-methoxyphenyl, 4-methoxyphenyl, 2,6-dimethoxyphenyl, 2,4-dimethoxyphenyl, 2,6-diethoxyphenyl, 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2-nitrophenyl, 4-nitrophenyl, 2,4-dinitrophenyl, 2,6-dinitrophenyl, 4-dimethylaminophenyl, and 4-acetylphenyl.

3. The process for preparing an aromatic acylphosphine oxide (II) according to claim 1, wherein $R^2$ and $R^3$ are each independently selected from the group consisting of 2,4,4-trimethylpentyl, benzyl, p-chlorobenzyl, 2,4-dichlorobenzyl, p-methoxybenzyl, methoxy, ethoxy, n-propyloxy, isopropyloxy, n-butyloxy, isobutyloxy, sec-butyloxy, tert-butyloxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, vinyl, 1-propenyl, allyl, methallyl, 1,1-dimethylallyl, 2-butenyl, 2-hexenyl, 2-phenylvinyl, 2-methoxyvinyl, 2-ethoxyvinyl, 2-chlorovinyl, phenyl, tolyl, xylyl, α-naphthyl, β-naphthyl, 4-diphenylyl, 2-chlorophenyl, 3-chlorophenyl, 4-chlorophenyl, 2,4-dichlorophenyl, 2,6-dichlorophenyl, 2,4,6-trichlorophenyl, 2-methylphenyl, 3-methylphenyl, 4-methylphenyl, 2,4-dimethylphenyl, 2,6-dimethylphenyl, 2,4,6-trimethylphenyl, 2-ethylphenyl, 3-ethylphenyl, 4-ethylphenyl, 2,4-diethylphenyl, 2,6-diethylphenyl, 2-isopropylphenyl, 3-isopropylphenyl, 4-isopropylphenyl, 2-tert-butylphenyl, 3-tert-butylphenyl, 4-tert-butylphenyl, 2-methoxyphenyl, 3-methoxyphenyl, 4-methoxyphenyl, 2,4-dimethoxyphenyl, 2,6-dimethoxyphenyl, 2-ethoxyphenyl, 3-ethoxyphenyl, 4-ethoxyphenyl, methylnaphthyl, chloronaphthyl, ethoxynaphthyl, 2,6-dimethylphenyl, 2,4,6-trimethylphenyl, 2,4-dimethoxyphenyl, 2,6-dimethoxyphenyl, 2,4-dichlorophenyl, 2,6-dichlorophenyl, 2-nitrophenyl, 4-nitrophenyl, 2,4-dinitrophenyl, 2,6-dinitrophenyl, 4-dimethylaminophenyl, 4-acetylphenyl, 2,4,6-trimethylbenzoyl, 2,6-dimethoxybenzoyl, and 2,6-dichlorobenzoyl.

4. The process for preparing an aromatic acylphosphine oxide (II) according to claim 1, wherein said process is carried out in the absence of a catalyst.

5. The process for preparing an aromatic acylphosphine oxide (II) according to claim 4, wherein said process is carried out at a temperature above 100° C.

6. The process for preparing an aromatic acylphosphine oxide (II) according to claim 4, wherein said process is carried out at a temperature of from 100° C. to 240° C.

7. The process for preparing an aromatic acylphosphine oxide (II) according to claim 4, wherein said process is carried out at a temperature of from 120° C. to 240° C.

8. The process for preparing an aromatic acylphosphine oxide (II) according to claim 4, wherein said process is carried out at a temperature of from 140° C. to 240° C.

9. The process for preparing an aromatic acylphosphine oxide (II) according to claim 4, wherein said process is carried out at a temperature of from 160° C. to 240° C.

10. The process for preparing an aromatic acylphosphine oxide (II) according to claim 1, wherein said process is carried out in the presence of a catalyst.

11. The process for preparing an aromatic acylphosphine oxide (II) according to claim 10, wherein said process is carried out at a temperature above 80° C.

12. The process for preparing an aromatic acylphosphine oxide (II) according to claim 10, wherein said process is carried out at a temperature of from 80° C. to 240° C.

13. The process for preparing an aromatic acylphosphine oxide (II) according to claim 10, wherein said process is carried out at a temperature of from 100° C. to 240° C.

14. The process for preparing an aromatic acylphosphine oxide (II) according to claim 10, wherein said process is carried out at a temperature of from 120° C. to 240° C.

15. The process for preparing an aromatic acylphosphine oxide (II) according to claim 1, wherein said catalyst is present in an amount of from 5 mol. % to 100 mol. %, based on said aromatic carboxyphosphine (I).

16. The process for preparing an aromatic acylphosphine oxide (II) according to claim 1, wherein said catalyst is present in an amount of from 5 mol. % to 50 mol. %, based on said aromatic carboxyphosphine (I).

17. The process for preparing an aromatic acylphosphine oxide (II) according to claim 1, wherein said catalyst is present in an amount of from 10 mol. % to 30 mol. %, based on said aromatic carboxyphosphine (I).

18. The process for preparing an aromatic acylphosphine oxide (II) according to claim 1, wherein said catalyst is selected from the group consisting of Friedel-Crafts catalysts, Lewis-acidic ionic liquid catalysts, nucleophilic catalysts, acid chloride catalysts, acid anhydride catalysts, alkyl halide catalysts, halogen catalysts, Arbusov catalysts, catalysts possessing simultaneous Lewis-acidic and Lewis-basic properties, and transition metals exhibiting a high affinity for phosphorus.

19. The process for preparing an aromatic acylphosphine oxide (II) according to claim 1, wherein said catalyst is selected from the group consisting of Lewis-acidic ionic liquid catalysts, nucleophilic catalysts, acid chloride catalysts, acid anhydride catalysts, alkyl halide catalysts, halogen catalysts, catalysts possessing simultaneous Lewis-acidic and Lewis-basic properties, and transition metals exhibiting a high affinity for phosphorus.

20. The process for preparing an aromatic acylphosphine oxide (II) according to claim 1, wherein said catalyst is selected from the group consisting of aluminum trichloride ($AlCl_3$), iron(III) chloride ($FeCl_3$), aluminum tribromide ($AlBr_3$), zinc chloride ($ZnCl_2$), trifluoroacetic anhydride, KI, NaI, LiI, and trimethylsilyl cyanide.

21. The process for preparing an aromatic acylphosphine oxide (II) according to claim 18, wherein said catalyst is selected from the group consisting of aluminum trichloride ($AlCl_3$), trifluoroacetic anhydride, and KI.

22. The process for preparing an aromatic acylphosphine oxide (II) according to claim 1, wherein said catalyst is an acid chloride $R^1COCl$ or an acid anhydride $(R^1CO)_2O$ of an aromatic compound according to formula (IV):

(IV)

wherein $R^1$ is a $C_6$-$C_{12}$ aryl group, which is optionally substituted by at least one aryl, alkyl, aryloxy, alkyloxy, and/or heteroatom.

23. The process for preparing an aromatic acylphosphine oxide (II) according to claim 22, wherein $R^1$ is selected from the group consisting of phenyl, tolyl, xylyl, α-naphthyl, β-naphthyl, 2-chlorophenyl, 3-chlorophenyl, 4-chlorophenyl, 2,6-dichlorophenyl, 2,4-dichlorophenyl, 2,4,6-trichlorophenyl, 2-methylphenyl, 3-methylphenyl, 4-methylphenyl, 2,6-dimethylphenyl, 2,4-dimethylphenyl, 2,4,6-trimethylphenyl, 2-ethylphenyl, 3-ethylphenyl, 4-ethylphenyl, 2,6-diethylphenyl, 2,4-diethylphenyl, 2-isopropylphenyl, 3-isopropylphenyl, 4-isopropylphenyl, 2-tert-butylphenyl, 3-tert-butylphenyl, 4-tert-butylphenyl, 2-methoxyphenyl, 3-methoxyphenyl, 4-methoxyphenyl, 2,6-dimethoxyphenyl, 2,4-dimethoxyphenyl, 2,6-diethoxyphenyl, 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2-nitrophenyl, 4-nitrophenyl, 2,4-dinitrophenyl, 2,6-dinitrophenyl, 4-dimethylaminophenyl, and 4-acetylphenyl.

24. The process for preparing an aromatic acylphosphine oxide (II) according to claim 1, wherein a reaction time of said rearrangement reaction is from 5 minutes to 5 hours.

25. The process for preparing an aromatic acylphosphine oxide (II) according to claim 1, wherein a reaction time of said rearrangement reaction is from 10 minutes to 3 hours.

26. The process for preparing an aromatic acylphosphine oxide (II) according to claim 1, wherein a reaction time of said rearrangement reaction is from 15 minutes to 2 hours.

27. The process for preparing an aromatic acylphosphine oxide (II) according to claim 1, wherein said rearrangement reaction is optionally carried out in the presence of a solvent.

28. The process for preparing an aromatic acylphosphine oxide (II) according to claim 1, wherein said rearrangement reaction is carried out in the presence of a polar solvent.

29. The process for preparing an aromatic acylphosphine oxide (II) according to claim 1, wherein said rearrangement reaction is carried out at a pressure selected from sub-atmospheric pressure, atmospheric pressure, and super-atmospheric pressure.

30. The process for preparing an aromatic acylphosphine oxide (II) according to claim 27, wherein said rearrangement reaction is carried out at a pressure ranging from atmospheric pressure to a super-atmospheric pressure of up to 5 bar, wherein said pressure remains below the boiling point of said optional solvent.

31. The process for preparing an aromatic acylphosphine oxide (II) according to claim 1, wherein said rearrangement reaction is carried out under an inert atmosphere.

32. The process for preparing an aromatic acylphosphine oxide (II) according to claim 1, wherein said rearrangement reaction is carried out in a one-pot synthesis.

33. The process for preparing an aromatic acylphosphine oxide (II) according to claim 1, wherein said rearrangement reaction is carried out discontinuously, semi-continuously, or continuously, in two separate reactors.

34. The process for preparing an aromatic acylphosphine oxide (II) according to claim 1, wherein said process further comprises separating said aromatic acylphosphine oxide (II) from said aromatic carboxyphosphine (I) by distillation, crystallization, or extraction.

35. The process for preparing an aromatic acylphosphine oxide (II) according to claim 34, wherein said extraction is a liquid-liquid extraction carried out with a solvent system comprising a mixture of at least two immiscible solvents of varying polarity.

36. The process for preparing an aromatic acylphosphine oxide (II) according to claim 35, wherein said solvent system is selected from the group consisting of sulfolane/tetrabutylurea, sulfolane/hexane and methanol/n-heptane.

* * * * *